United States Patent

Choi et al.

[11] Patent Number: 5,935,997
[45] Date of Patent: Aug. 10, 1999

[54] O-THIOCARBAMOYL-AMINOALKANOL COMPOUNDS, THEIR PHARMACEUTICALLY USEFUL SALTS AND PROCESS FOR PREPARING THE SAME

[75] Inventors: Yong Moon Choi, Towaco, N.J.; Yong Kil Kim, Taejon, Rep. of Korea

[73] Assignee: Yukong Limited, Seoul, Rep. of Korea

[21] Appl. No.: 09/006,528

[22] Filed: Jan. 13, 1998

[51] Int. Cl.$^6$ .......................... A61K 31/27; C07C 333/04
[52] U.S. Cl. .......................... 514/478; 514/489; 514/423; 514/255; 514/237.5; 544/358; 544/389; 544/159; 544/160; 548/331; 558/234
[58] Field of Search .......................... 558/234; 548/331; 544/358, 389, 159, 160; 514/478, 489, 423, 255, 237.5

[56] References Cited

U.S. PATENT DOCUMENTS 2,901,501  8/1959  Wasson et al. .......................... 260/455

OTHER PUBLICATIONS

CA:55, 545e, 1961.

*Primary Examiner*—Shailendra Kumar
*Attorney, Agent, or Firm*—Gibbons, Del Deo, Dolan, Griffinger & Vecchione

[57] ABSTRACT

The present invention relates to O-thiocarbamoyl-aminoalkanol compound represented by the following structural formula (VI), (VIII) and (IX) which are a racemic or enantiomerically enriched and pharmaceulically acceptable salts thereof to treat diseases of the central nervous system:

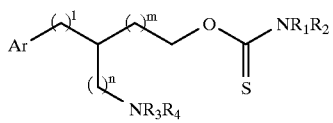

(VI)

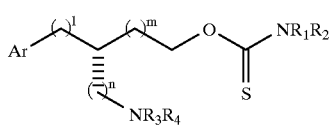

(VIII)

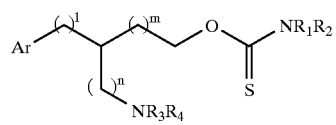

(IX)

wherein Ar is a phenyl group as described as follows:

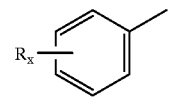

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or taifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_{1\ and\ R2}$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membercd aliphatic cyclic compounds and $R_3$ and $R_4$, together with the adjoining N-atom, form a 5 to 7-membered cyclic compound which optidonally comprises zero to one additional nitrogen atoms substituted with a member selected from the group consisting of hydrogen, alkyl and aryl groups, or zero to one oxygen atoms directly unconnected, each of l, m and n is zero or 1, and the pharmaceutically acceptable salts thereof.

88 Claims, No Drawings

O-THIOCARBAMOYL-AMINOALKANOL COMPOUNDS, THEIR PHARMACEUTICALLY USEFUL SALTS AND PROCESS FOR PREPARING THE SAME

BACKGROUND OF THE INVENTION

1. Field of the Invention

The present invention relates, in general, to novel thiocarbamates of aminoalkanols and pharmaceutically useful salts thereof, useful in the treatment of the diseases of the central nervous system. More particularly, the present invention relates to racernic mixture or enantiomerically enriched O-thiocarbamoyl-aminoalkanol compounds and pharmaceutically useful salts thereof, processes for their production, compositions thereof and methods of treating central nervous system disorders.

2. Description of the Prior Art

Phenylethylamine derivatives, one important class of therapeutical medicines useful in managing central nervous system (CNS) diseases, have been used mainly to treat obesity, narcolepsy, minimal brain dysfunction and mild depression.

Organic thiocarbwnates or carbamates have been effectively used for controlling various CNS disorders. For example, U.S. Pat. No. 2,901,501 discloses 1,3-dithiocarbamoyl-1,3-propanediols that are further substituted at position-2 with hydrocarbon based moieties that include aryl groups. J. Am. Chem. Soc., 73, 5779 (1951) discloses 2-methyl-2-propyl-1,3-propandiol dicarbamate and its pharmaceutical activity was verified in J. Pharmacol. Exp. Ther., 104, 229 (1952). Besides, there are many carbamate compounds that are suggested as therapeutics for CNS disease in the prior art. For example, U.S. Pat. Nos. 2,884,444 and 2,937,119 disclose carbamates, such as 2-phenyl-1,3-propandiol dicarbamate and isopropylmeprobamate, respectively. These compounds are found to be very effectively used as therapeutics for treating CNS disorders, especially as antiepileptic and centrally acting muscle relaxants. Research in the development of thiocarbamate or carbamate therapeutics for CNS diseases has been and continues to be actively advanced.

Recent design of pharmacologically useful compounds has been based on amino acids or the derivatives thereof, which is mainly attributable to the fact that many of the compounds found in biological systems come from amino acids or the derivatives thereof In addition, in most cases, the function of a pharmaceutically usefuil compound is effected after it binds to an enzyme or receptor, which may trigger the regulatory mechanisms of the enzyme or receptor.

SUMMARY OF THE INVENTION

As a result of intensive and thorough research, it has been found that O-thiocarbamoyl-aminoalkanol compounds are pharmaceutically useful for CNS disorders, especially for depression and anxiety. Accordingly, it is a principal object of the present invention to provide racemic O-thiocarbamoyl-aminoalkanol compounds, represented by the following general structural formula (VI):

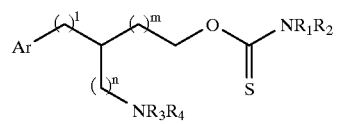

(VI)

wherein Ar is a phenyl group as described as followings:

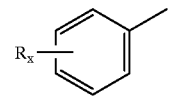

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be same or different from each other and are independently selected from the group consisting of hydrogen, lower alkyl from 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atom substituted with a member selected from the group consisting of hydrogen, alkyl and aryl groups, or zero to one oxygen atom directly unconnected. $R_3$ and $R_4$ may be same or different from each other and are independently selected from the group consisting of hydrogen, lower alkyl from 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atom substituted with a member selected from the group consisting of hydrogen, alkyl and aryl groups, or zero to one oxygen atom directly unconnected. Each of 1, m and n is zero or 1, and the pharmaceutically acceptable salts thereof.

It is also a principal object of the present invention to provide O-thiocarbamoyl-(D)-aminoalkanol compounds, represented by the following structural formula VIII; (alternatively, "D" can be referred to as the R-configuration at the chiral center in structural formula VIII)

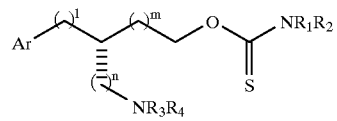

(VIII)

wherein Ar is a phenyl group as described as follows:

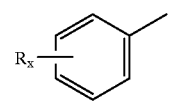

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyl from 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atom substituted with a member selected from the group consisting of hydrogen, alkyl and aryl groups, or zero to one oxygen atoms directly unconnected. $R_3$ and $R_4$ may be same or different from each other and are independently selected from the group consisting of hydrogen, lower alkyl from 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and amyl groups, or zero to one oxygen atom directly unconnected. Each of 1, m and n is zero or 1, and the pharmaceutically acceptable salts thereof.

It is also a principal object of the present invention to provide O-thiocarbamoyl-(L)-aminoalkanol compounds, represented by the following structural formula IX: (alteratively, "L" can be referred to as the S-configuration at the chiral center in structural formula (IX)

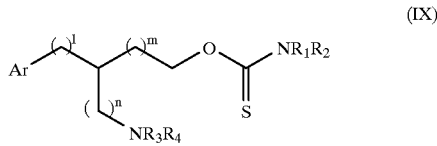

wherein Ar is a phenyl group as described as follows:

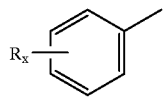

wherein R is a member selected from the group consisting of hydrogen, lower alkyl of 1 to 8 carbon atoms, halogen selected from F, Cl, Br, and 1, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atorn, form a 5 to 7-membered cyclic compound which may comprise zero to one additional nitrogen atom substituted with a member selected from the group consisting of hydrogen, alkyl and aryl groups, or zero to one oxygen atom directly unconnected. $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which may comprise zero to one additional nitrogen atom substituted with a member selected from the group consisting of hydrogen, alkyl and aryl groups, or zero to one oxygen atom directly unconnected. Each of 1, m and n is zero or 1, and the pharmaceutically acceptable salts thereof.

DETAILED DESCRIPTION OF THE INVENTION

In accordance with the present invention, the racemic or enantiomerically enriched O-thiocarbamoyl-aminoalkanols represented by the structural fornula VI, VIII and IX and pharmaceutically acceptable salts thereof can be prepared by the following steps starting from readily available starting materials represented by the following general structural formula II:

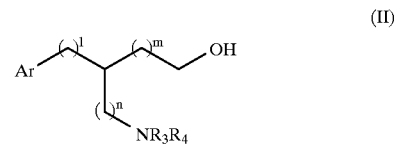

wherein Ar is the same as defined above.

It should be noted that the stereochemistry of the final products (VI, VIII and IX) depend solely on that of the starting material (II); a starting material (II) with an D-enantiomer yields only a product with D-enantiomer (VIII) and a starting material (II) with an L-enantiomer yields only a product with L-enantiomer (IX)

The first method for preparing the novel compounds of the general formula VI in which $R_3=R_4=H$ or $R_4=H$ will be described below in detail.

Initially, aminoalkanol (11) is reacted with Di-t-butyl dicarbonate to synthesize N-t-butyloxycarbonyl-atninoalkanol represented by the general formula (III).

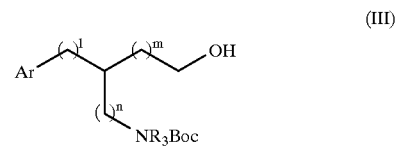

This is followed by the treatment with sodium hydride, carbon disulfide and methyl iodide in an ethereal solution which is followed by the treatment with an amine base (IV) to yield O-thiocarbarnoyl-N-t-butyloxycarbonyl-aminoalkanol represented by the general formula (V):

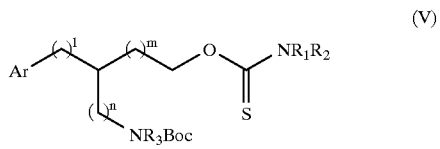

wherein Ar, $R_1$, $R_2$, $R_3$, $R_4$, 1, m and n are as defined above and Boc represents t-butylDxy carbonyl radical. Then, this intermediate is deprotected by aqueous hydrochloric acid solution. As a result of the deprotection, there is obtained O-thiocarbamoyl-aminoalkanol represented by the general formula VI. Without further purification, the compound of formula VI may be converted into pharmaceutically acceptable salts (I) as described above.

This procedure is sum.ied as set forth in Reaction Scheme I below.

Reaction Scheme I

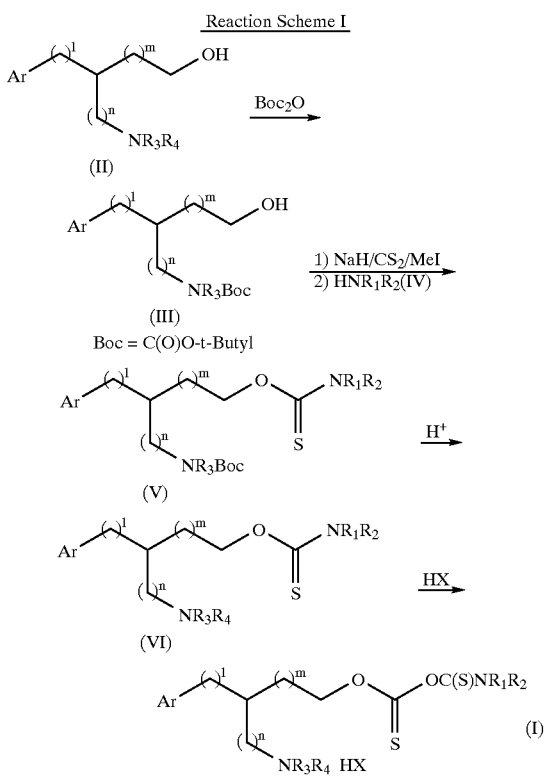

Details of the reaction conditions described in Reaction Scheme I are as follows. In the first step, the concentration of the starting mnaterial (II) is about 0.005 to 3 moles with di-t-butyl dicarbonate ranging from about 1.0 to 2.0 equivalents. The basic aqueous solution has a pH value between about 7 and 14 and the conversion is carried out at temperature from about −10 to 70° C. For the conversion of the compound (III) to the compound (IV), sodium hydride and carbon disulfide ranging from about 1.0 to 2.0 equivalents and methyl iodide ranging from about 1.0 to 2.5 equivalent is used and is preferably carried out at a temperature of about −10 to 70° C. Without purification, the resulting intermediate is treated with 1to 5 equivalents of amiine at a temperature of about −10 to 30° C., to give the compound of the general formula (V). For this thiocarbamoylation, an ethereal solvent, such as diethyl ether and tetrahydrofuiran, or a polar aprotic solvent, such as dimethylformnmide and dimethyl sulfoxide, is employed. The compound of the general formula (VI) (0.005 to 3 moles) is treated with aqueous 1 to 12N hydrochloric acid at a temperature of about −10 to 30° C., followed by neutralization.

In the Reaction Scheme I, HX represents an acid capable of formng a pharmacologically useful salt with the basic nitrogen atom. Specific examples of the anhydrous acid used for the preparation of the compound (I) from the compound (VI) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid and the like. Additional acids can refer to "Pharmaceutical Salts", J. Pharm. Sci., 1977; 66 (1): 1–19. This preparation is executed in a reaction media which can be exemplified by an ethereal solvent such as THF, an alcoholic solvent such as methanol, an ester solvent such as ethyl acetate, an aromatic solvent, and any compositional mture thereof An ethereal solvent is recommended as an addition solution, including ethyl ether, propyl ether, isopropyl ether, butyl ether, isobutyl etber. The concentration of the compound (VI) is on the order of about 0.01 to 5 mole.

The second method for preparing the novel compounds of the general formula (VI) in which $R_3$ and $R_4$ are not hydrogen will be described in detail below.

Initially, aniinoallanol (II) is reacted with sodium hydride, carbon disulfide and methyl iodide in an ethereal solution resulting in a xanthate which is, then, treated with an amine base (IV) to yield O-thiocarbamoyl-aminoalkanol represented by the general formula (VI)

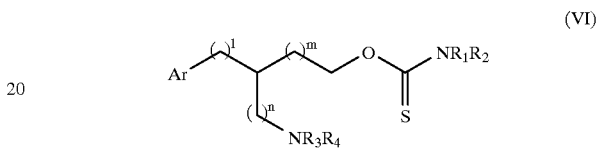

wherein Ar, $R_1$, $R_2$, $R_3$, $R_4$, l, m and n are as defined above. Without further purification, the compound of formula (VI) may be conveited into pharmaceutically acceptable salts (I) as described above.

This procedure is summarized as set forth in Reaction Scheme II below.

Reaction Scheme II

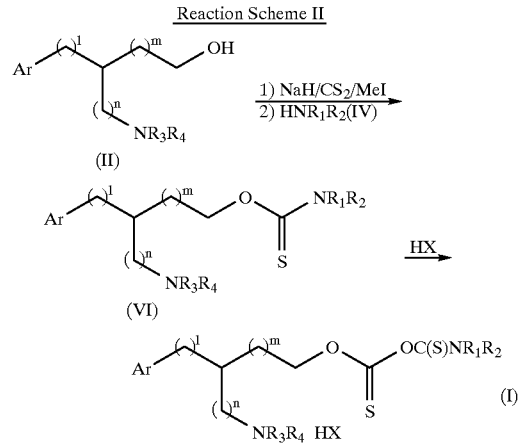

Details of the reaction conditions described in Reaction Scheme I are as follows. In the first step, for the conversion of the compound (II) to the compound (VI), sodium hydride and carbon disulfide ranging from about 1.0 to 2.0 equivalents and methyl iodide ranging from about 1.0 to 2.5 equivalents is used and is preferably carried out at a temperature of about −10 to 70° C. Without purification, the resulting intermediate is treated with 1 to 5 equivalents of amine(IV) at a temperature of about −10 to 30° C., to give the compound of the general fornula (VI). For this thiocarbamoylation, an ethereal solvent, such as diethyl ether and tetrahydrofaran, or a polar aprotic solvent ,such as dimethylformamide and dimethyl sulfoxide, is employed. The compound of the general formula (VI) (about 0.005 to 3 moles) is treated with aqueous 1 to 12N hydrochloric acid at a temperature of about −10 to 30° C., followed by neutralization.

In the Reaction Scheme II, HX represents an acid capable of forming a pharmacologically useful salt with the basic nitrogen atom.

The third method for preparing the novel compounds of the general formula (VI) in which $R_1=R_3=R_4=H$ or $R_1=R_4=H$ will be described in detail below.

Initially, reacting N-(t-butyloxycarbonyl)-aminoalkanol (III) with isothiocyanate (VII) yields a N-(t-butyloxycarbonyl)-O-thiocarbamoyl-aminoalkanol represented by the general formula (V):

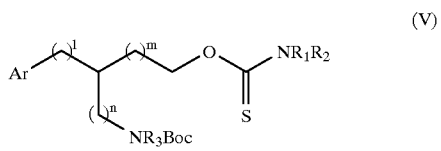

wherein Ar, $R_1$, $R_2$, $R_3$, l, m and n are as defined above and Boc repressants t-butyloxy carbonyl radical. Then, this intermediate is deprotected by aqueous hydrochloric acid solution. As a result of the deprotection, there is obtained O-thiocarbamoyl-aminoalkanol represented by the general formula (VI). Without farther purification, the compound of formula (VI) may be converted into pharmaceutically acceptable salts (I) as described above.

This procedure is summarized as set forth in Reaction Scheme III below.

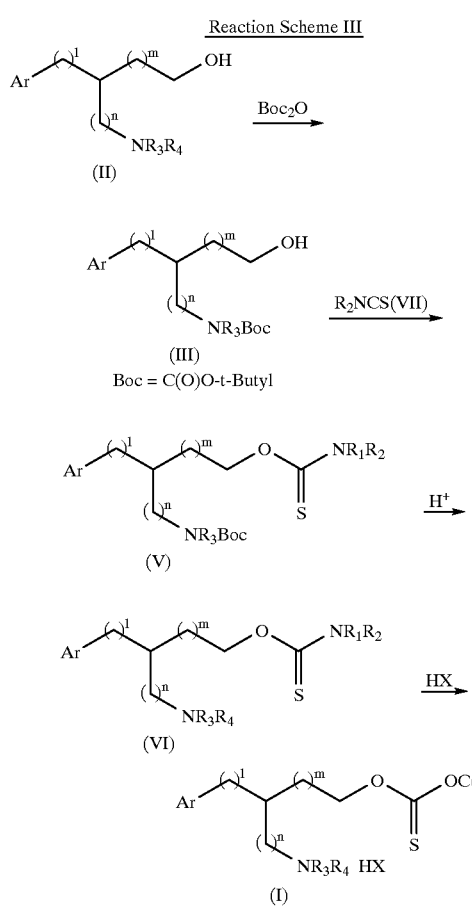

Details of the reaction conditions described in Reaction Scheme III are as follows. In the second step, the concentration of the starting material (III) is about 0.005 to 3 moles with isothiocyanate (VII) ranging from about 1.0 to 2.0 equivalents. The conversion is carried out at temperature from about 30 to 110° C. For this thiocarbamoylation, an ethereal solvent such as diethyl ether and tetrahydrofuran, a halogenated hydrocarbon solvent, such as dichloromethane and chloroform or an aromatic solvent, such as benzene and toluene may be used, with the halogenated hydrocarbon solvent, such as dichloromethane and chloroform being preferred. The compound of the general formula (VI) (about 0.005 to 3 moles) is treated with aqueous 1 to 12 N hydrochloric acid at a temperature of about −10 to 30° C., followed by neutralization.

The fourth method for preparing the novel compounds of the general formula (VI) in which $R_3$ and $R_4$ are not hydrogen and $R_1$ is hydrogen will be described in detail below.

Initially, aniinoalkanol (II) is reacted with isothiocyanate (VII) in a halogenated hydrocarbon solvent to yield a O-thiocarbamoyl-aminoalkanol represented by the general formula (VI):

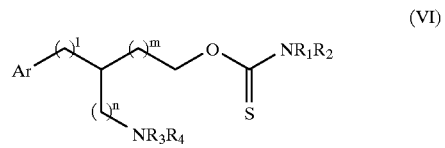

wherein Ar, $R_1$, $R_2$, $R_3$, l, m and n are as defined above. Without further purification, the compound of formula (VI) may be converted into pharmaceutically acceptable salts (I) as described above.

This procedure is summarized as set forth in Reaction Scheme IV below.

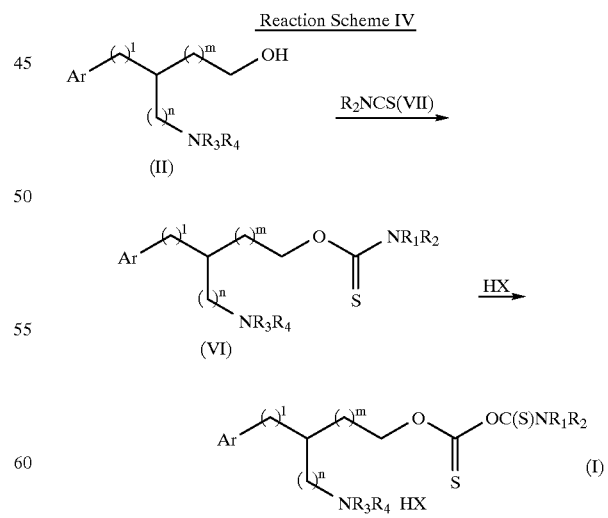

Representative examples of the compounds (VI), (VIII) and (IX) from Reaction Scheme I, II, III and IV are shown in Table I:

TABLE I

Examples of the compound (VI), (VIII) and (IX) from Reaction Scheme I, II, III and IV

| Rx | R₁ | R₂ | R₃ | R₄ | Rx | R₁ | R₂ | R₃ | R₄ |
|---|---|---|---|---|---|---|---|---|---|
| H | H | H | H | H | H | Me | Me | H | H |
| H | H | Me | H | H | H | Et | Et | H | H |
| H | H | Et | H | H | H | H | i-Pr | H | H |
| H | H | n-Pr | H | H | H | H | n-Bu | H | H |
| H | H | c-Pr | H | H | H | H | c-Hex | H | H |
| H | H | n-Oct | H | H | H | H | C6H5 | H | H |
| H | H | benzyl | H | H | H | H | o-F—C6H5 | H | H |
| H | H | COOEt | H | H | H | — | pyrrolidinyl | H | H |
| H | — | morpholinyl | H | H | H | — | N-methylpiperazinyl | H | H |
| o-F | H | Me | H | H | p-Cl | H | H | H | H |
| m-F | H | H | H | H | p-Cl | H | Me | H | H |
| p-F | H | H | H | H | p-MeS | H | H | H | H |
| p-OH | H | H | H | H | p-MeO | H | H | H | H |
| 3,4-(HO)2 | H | H | H | H | m,p-(Cl)2 | Me | Me | H | H |
| 3,4-(MeO)2 | H | H | H | H | 3,4-(HO)2 | Me | Me | H | H |
| H | H | Me | Me | H | H | H | i-Pr | Me | Me |
| p-F | H | Me | Me | H | p-HO | H | H | Me | Me |
| H | H | Me | i-Pr | H | H | H | Me | Me | Me |
| m-F | H | H | i-Pr | H | p-MeO | H | H | Me | Me |
| H | H | COOEt | Benzyl | H | p-Cl | H | Me | Benzyl | H |

For therapeutic use in medicines for treating pain, depression, anxiety, epilepsy, stroke, demential and Parkinson's disease, the compounds of the present invention, alone or in combination with a pharmaceutically acceptable carrier, are administered to patients at a dosage of from about 0.7 to 7,000 mg per day. For a normal human adult with a body weight of approximately 70 kg, the administration amount is translated into a daily dose of about 0.01 to 100 mg per kg of body weight. The specific dosage employed, however, will vary depending upon the requirements of the patient, the severity of the patient's condition and the activity of the compound. The determination of optimum dosages for a particular situation must be determined clinically and is within the skill of the art.

In utilizing the compounds of the present invention for the treatment of disorders and diseases of the central nervous system, particularly to treat depression, it is preferred to administer the compounds orally. Since the compounds are well-absorbed orally, it usually will not be necessary to resort to parenteral administration. For oral administration, the compound (I) of female is preferably combined with a pharmaceutical carrier. The ratio of the carrier to the compound of Formula (I) is not critical to express the effects of the medicine on the central nervous system, and it can vary considerably depending on whether the composition is to be filled into capsules or formed into tablets. In tableting, various edible pharmaceutical carriers or mixtures thereof can be used. Suitable carriers, for example, are a niiture of lactose, diabasic calcium phosphate and/or corn starch. Other pharmaceutically acceptable ingredients can be further added, including lubricants such as magnesium stearate.

Besides the compound of Formula (I), compositions comprising it are within the scope of the present invention. Furthermore., the present invention includes uses of the compound (I) and/or the composition.

As described hereinbefore, the compounds represented by Structural Formula I were observed to be useful for the prophylaxis and treatment of CNS disorders including pain, depression, anxiety, epilepsy, stroke, demential and Parkinson's disease. The therapeutic use of the compounds claimed in the present invention as antidepressants has been proven by the "Forced Swinuning Test", a well known pharmacological screening methods for depression and the results are shown in the following Table II. The procedure described by Porsolt et al., (1997) was used. Test compound was administered p.o. and i.p. to mice (CD-1 strain), one hour prior to the animals being immersed in a 1500 mL glass beaker (16.5 cm deep, 13.0 cm diameter) filled with water (20~23° C.) to about 5 cm from the top. Mice were kept in the water for a period of 15 minutes and the duration of immobility observed within the 15-minute test period was recorded. A mouse was judged to be immobile if it floated motionlessly in the water making only those movements necessary to keep its head above the water.

TABLE II

| Compound | Dose (mg/kg) | Inhibition (reduction, %) |
|---|---|---|
| (2S)-2-amino-3-phenylpropyl carbamothioate·HCl (benzyl, S-config, OC(=S)NH₂, NH₂·HCl) | i.p. (30 mg/kg)<br>p.o. (30 mg/kg) | 41.6<br>— |
| (2R)-2-amino-3-phenylpropyl carbamothioate·HCl (benzyl, R-config, OC(=S)NH₂, NH₂·HCl) | i.p. (30 mg/kg)<br>p.o. (30 mg/kg) | 51.2<br>— |
| 3-amino-2-phenylpropyl N-methylcarbamothioate·HCl (NH₂HCl-CH₂, phenyl on C2, OC(=S)NHCH₃) | i.p. (30 mg/kg)<br>p.o. (30 mg/kg) | 30.5<br>25.6 |
| 2-amino-3-(4-chlorophenyl)propyl carbamothioate·HCl | i.p. (30 mg/kg)<br>p.o. (30 mg/kg) | 30.6<br>38.1 |
| 2-(dimethylamino)-3-phenylpropyl N-methylcarbamothioate | i.p. (30 mg/kg)<br>p.o. (30 mg/kg) | 31.4<br>23.4 |
| (2S)-2-amino-3-(3,4-dichlorophenyl)propyl N,N-dimethylcarbamothioate·HCl | i.p. (30 mg/kg)<br>p.o. (30 mg/kg) | 54.9<br>50.8 |
| 3-amino-3-phenylpropyl N-methylcarbamothioate·HCl | i.p. (30 mg/kg)<br>p.o. (30 mg/kg) | 44.2<br>29.2 |

The therapeutic use of the compounds claimed in the present invention as anticonvulsants has been proven by the "Maxmal ElectroShock (MES)" test, which is a well-established pharmacological screening method for anticonvulsants against partial seizures, and the results are presented in Table III.

The procedure employed in the MES test for anticonvulsants follows. The compound dosing solutions were prepared in saline, and the subject, namely, mice (CD-1strain), were dosed orally. After the designated number of hours, maximal electroshock was induced in mice via corneal electrodes using IITC Life Science model 11A Shocker at 50mA-60 Hz for 0.2 second. Upon inducing maximal electroshock, the elimination of hindlimb tonic extension was considered as providing evidence of the protection by an anticonvulsant. Median efficacy dose (ED50) levels were detennined using three different dose levels with at least 6 mice in each group. Compounds with smaller ED50 value are more potent as anticonvulsants.

TABLE III

| Compound | MES (ip, 30 mg/kg) or ED50 | MES (po, 30 mg/kg) or ED50 |
| --- | --- | --- |
| [Structure: benzyl-CH2-CH(NH2·HCl)-CH2-O-C(=S)-NH2] | ED50 = 29.0 (0.5 h) | ED50 = 188.8 (0.5 h) |
| [Structure: benzyl-CH2-CH(NH2·HCl)-CH2-O-C(=S)-NHMe] | ED50 = 20.9 (1 h) | 3/3 (0.5 h) |
| [Structure: 2-F-benzyl-CH2-CH(NH2·HCl)-CH2-O-C(=S)-NHMe] | ED50 = 24.7 (1 h) | — |
| [Structure: benzyl-CH2-CH(NH2·HCl)-CH2-O-C(=S)-NHMe, (S)-config] | ED50 = 41.8 (0.5 h) | ED50 = 152.0 (0.5 h) |
| [Structure: benzyl-CH2-CH(N(CH3)2)-CH2-O-C(=S)-NHCH3] | ED50 = 31.5 (1 h) | ED50 = 82.5 (0.5 h) |
| [Structure: 3,4-diCl-benzyl-CH2-CH(NH2·HCl)-CH2-O-C(=S)-N(CH3)2] | 1/3 (4.0 h) | — |

A better understanding of the present invention may be obtained in light of following examples which are set forth to illustrate, but are not to be construed to limit, the present invention.

EXAMPLE 1

O-Thiocarbamoyl-N-(t-butyloxycarbonyl)-(DL)-phenylalaninol

In a 500 mL flask equipped with magnetic stirrer, N-(t-butyloxycarbonyl)-(DL)-phenylalaninol(0.051 mole, 13.6 g) was dissolved in 200 mL of THF and was added with NaH(0.061 mole, 1.47 g) at 0° C. The reaction mixture was stirred at 0° C. for 1 hour, followed by the addition of CS$_2$(0.061 mole, 4.66 g). After being stirred for 40 min. at 0° C., MeI(0.061 mole, 8.69 g) was added to the reaction mnixture. The reaction mixture was stirred at room temperature for 2 hours, followed by the addition of 5N NH$_4$OH (0.090 mole, 18.0 mL) for 6 hours. The resulting solution was quenched with water. The organic layer was extracted 3 times with dichloromethane, dried over magnesium sulfate and distilled in vacuo, to give a solid. This was recrystalized in a solution mixture-of n-hexane and diethyl ether, to produce 14.7 g of O-thiocarbamoyl-N-(t-butyloxycarbonyl)-(DL)-phenylalaninol: Yield 80%.

$_1$H-NMR(CDCl$_3$, 200 MHz), ppm(δ); 1.35(s,9H), 2.65–2.98(m,2H), 4.05–4.25(br,1H), 4.33–4.43(m,2H), 4.62–4.83(br,1H), 6.25(s,1H), 6.58(s,1H), 7.01–7.42(m,5H).

EXAMPLE 2

O-Thiocarbamoyl-N-(t-butyloxycarbonyl-(L)-phenylalaninol

The procedure given in Example 1was followed using N-(t-butyloxycarbonyl)-(L)-phenylalaninol as a starting material, instead of N-(t-butyloxycarbonyl)-(DL)-phenylalaninol, to give 1.90 g of the title compound. A yield of 79% was obtained.

$_1$H-NMR(CDCl$_3$, 200 MHz), ppm(δ); 1.38(s,9H), 2.72–2.95(m,2H), 4.01–4.28(br,1H), 4.30–4.48(m,2H), 4.62–4.83(br,1H), 6.22(s,1H), 6.67(s,1H), 7.08–7.39(m,5H).

EXAMPLE 3

O-Thiocarbamoyl-N-(t-butyloxycarbonyl)-(D)-phenylalaninol

In a 500 mL flask equipped with magnetic stirrer, N-(t-butyloxycarbonyl)-(D)-phenylalaninol(0.040 mole, 10.05 g) was dissolved in 200 mL of THf and was added with NaH(0.048 mole, 1.15 g) at 0° C. The reaction mixture was stirred at 0° C. for 1 hour, followed by the addition of $CS_2$(0.048 mole, 3.65 g). After being stirred for 40 min. at 0° C., MeI(0.048 mole, 6.81 g) was added to the reaction mixture. The reaction mixture was stirred at room temperature for 2 hours, followed by the addition of 5N $NH_4OH$ (0.090 mole, 18.0 mL) for 6 hours. The resulting solution was quenched with water. The organic layer was extracted 3 times with dichloromethane, dried over magnesium sulfate and distilled in vacuo, to give a solid. This was recrystalized in a solution mixture of n-hexane and diethyl ether, to produce 11.3 g of O-thiocarbamoyl-N-(t-butyloxycarbonyl)-(D)-phenylalaninol: Yield 78%.

$_1$H-NMR(CDCl$_3$, 200 MHz), ppm($\delta$); 1.45(s,9H), 2.77–3.01(m,2H), 4.01–4.28(br,1H), 4.30–4.51(m,2H), 4.60–4.83(br,1H), 6.25(s,1H), 6.55(s,1H), 7.11–7.51(m,5H).

EXAMPLE 4

O-(N-Methyl)thiocarbamoyl-N-(t-butyloxncarbonyl (D)-phenylalaninol

The procedure given in Example 3 was followed using methylamine as a reactant, instead of $NH_4OH$, to give 2.33 g of the tide compound. A yield of 75% was obtained.

$_1$H-NMR(CDCl$_3$, 200 MHz), ppm($\delta$); 1.45(s,9H), 2.68–2.98(m,2.5H), 3.12(d,1.5H), 4.06–4.28(br,1H), 4.31–4.55(m,2H), 6.35(br,0.5H), 6.65(br,0.5H), 7.05–7.48 (m5H).

EXAMPLE 5

O-(N-Cyclopropl)thiocarbamoyl-N-(t-butyloxycarbonyl)-(D)-phenylalaninol

The procedure given in Example 3 was followed using cyclopropylamine as a reactant, instead of $NH_4OH$, to give 2.49 g of the title compound. A yield of 74% was obtained.

$_1$H-NMR(CDCl$_3$, 200 MHz), ppm($\delta$); 0.51–0.98(m,4H), 1.45(s,9H), 2.68–3.05(m,3H), 4.05–4.82(m,4H), 6.42(br, 0.5H), 6.82(br,0.5H), 7.05–7.48(m,5H).

EXAMPLE 6

O-(N-Octyl)thiocarbamoyl-N-(t-butyloxycarbonyl)-(D)-phenylalaninol

The procedure given in Example 3 was followed using n-octylamine as a reactant, instead of $NH_4OH$, to give 3.34 g of the title compound. A yield of 78% was obtained.

$_1$H-NMR(CDCl$_3$, 200 MHz), ppm($\delta$); 0.89(t,3H), 1.02–1.78(m,21H), 2.68–3.02(m,2H), 3.25(q,1H), 3.52(q, 1H), 4.01–4.82(m,4H), 6.45(br,0.5H), 6.95(br,0.5H), 7.05–7.48(m,5H).

EXAMPLE 7

O-(N-Isopropyl)thiocarbamoyl-N-(t-butyloxycarbonyl)-(D)-phenylalaninol

The procedure given in Example 3 was followed using isopropylaniine as a reactant, instead of $NH_4OH$, to give 3.0 g of the title compound. A yield of 80% was obtained.

$_1$H-NMR(CDCl$_3$, 200 MHz), ppm($\delta$); 1.12–1.65(m,15H), 2.72–2.955(m,2H), 4.05–4.55(m,3H), 4.65(br,1H), 6.15(br, 0.5H), 6.52(br,0.5H), 7.05–7.48(m,5H)

EXAMPLE 8

O-(N-Dimethyl)thiocarbamoyl-N-(t-butyloxycarbonyl)-(D)-phenylalaninol

The procedure given in Example 3 was followed using dimethylamine as a reactant, instead of $NH_4OH$, to give 2.56 g of the title compound. A yield of 67% was obtained.

$_1$H-NMR(CDCl$_3$, 200 MHz), ppm($\delta$); 1.45(s,9H), 2.78–2.98(m,2H), 3.12(s,3H), 3.38(s,3H), 4.18–4.52(m,3H), 4.58–4.74(br,1H), 7.10–7.38(m,5H).

EXAMPLE 9

O-(N-Morpholino)thiocarbamoyl-N-(t-butyloxycarbonyl)-(D)-phenylalaninol

The procedure given in Example 3 was followed using morpholine as a reactant, instead of $NH_4OH$, to give 2.97 g of the title compound. A yield of 75% was obtained.

$_1$H-NMR(CDCl$_3$, 200 MHz), ppm($\delta$); 1.45(s,9H), 2.68–2.98B(m,2H), 3,55–3.92(m,6H), 4.01–4.75(m,6H), 7.05–7.48(m,5H).

EXAMPLE 10

O-(N-Methyl)thiocarbamoyl-N-(t-butyloxycarbonyl)-(DL)-(o-fluoro)phenylalaninol

The procedure given in Example 1 was followed using N-(t-butyloxycarbonyl)-(DL)-(o-fluoro)phenylalaninol as a starting material and methylamine as a reactant, instead of N-(t-butyloxycarbonyl)-(DL)-phenylalaninol and $NH_4OH$, to give 1.01 g of the title compound. A yield of 60% was obtained.

$_1$H-NMR(CDCl$_3$, 200 MHz), ppm($\delta$); 1.35(s,9H), 2.72–3.15(m,5H), 4.01–4.28(br,1H), 4.30–4.52(m,2H), 4.58–4.83(br,1H), 6.42(s,1H), 6.71(s,1H), 6.98–7.32(m,5H).

EXAMPLE 11

O-Thiocarbamoyl-N-(t-butyloxycarbonyl)-(DL)-(p-chloro)phenylalaninol

The procedure given in Example 1 was followed using N-(t-butyloxycarbonyl)-(DL)-(p-chloro)phenylalaninol as a starting material, instead of N-(t-butyloxycarbonyl)-(DL)-phenylalaninol, to give 3.0 g of the title compound. A yield of 62% was obtained.

$_1$H-NMR(DMSO-d$_6$, 200 MHz), ppm($\delta$); 1.32(s,9H), 2.62–2.82(m,2H), 3.79–4.01(br,1H), 4.03–4.42(m,3H), 6.98–7.42(m,5H), 8.25(s,1H), 8.65(s,1H).

EXAMPLE 12

O-Thiocarbamoyl-N-(t-butyloxycarbonyl)-(D)-(t-butyloxycarbonyloxy)phenylalaninol The procedure given in Example 3 was followed using N-(t-butyloxycarbonyl)-(D)-(t-butyloxycarbonyloxy) phenylalaninol as a starting material, instead of N-(t-butyloxycarbonyl)-(D)-pbenylalaninol, to give 2.9 g of the title compound. A yield of 60% was obtained.

$_1$H-NMR(CDCl$_3$, 200 MHz), ppm($\delta$); 1.18–1.75(m,18H), 2.78–3.01(m,2H), 4.11– 4.25(m,1H), 4.35–4.51(m,2H), 4.65–4.85(m,1H), 6.22(br.s,1H), 6.66(br.s,1H), 7.02–7.35 (m,4H).

EXAMPLE 13

O-(N-Dimethyl)thiocarbamoyl-N-(t-butyloxycarbonyl)-(D)-(m,p-dichloro)phenylalaninol The procedure given in Example 3 was followed using N-(t-butyloxycarbonyl)-(D)-(m,p-dichloro)phenylalaninol as a starting material and dimethylamine as a reactant, instead of N-(t-butyloxycarbonyl)-D)-phenylalaninol and NH$_4$OH, to give 2.5 g of the title compound. A yield of 62% was obtained.

$_1$H-NMR(CDCl$_3$, 200 MHz), ppm($\delta$); 1.28–1.42(m,9H), 2.69–2.88(m,2H), 3.11(d,3H), 3.37(d,3H), 4.09–4.28(m, 1H), 4.35–4.51(m,2H), 4.61–4.81(m,1H), 7.01–7.41(m,3H).

EXAMPLE 14

O-(N-Ethoxycarbonyl-)thiocarbamoyl-N-(t-butyloxycarbonyl)-(D)-phenylalaninol In a 100 mL flask equipped with magnetic stirrer, N-(t-butyloxycarbonyl)-(D)-phenylalaninol(0.013 mole, 3.3 g) was dissolved in 50 mL of chloroform and was added with ethoxycarbonyl isothiocyanate(0.014 mole, 1.7 mL) at room temperature. The reaction mixture was heated under reflux for 6 hours and then cooled to room temperature. The resulting solution was quenched with water. The organic layer was extracted 3 times with dichloromethane, dried over magnesium sulfate and distilled in vacuo, to give a solid. This was recrystalized in a solution mixture of n-hexane and diethyl ether, to produce 2.56 g of O-(N-ethoxycarbonyl)thiocarbamoyl-N-(t-butyloxycarbonyl)-(D)-phenylalaninol. A yield of 56% was obtained.

$_1$H-NMR(CDCl$_3$, 200 MHz), ppm($\delta$); 1.18–1.61(m,12H), 2.82–3.08(m,2H), 4.22–4.38(m,3H), 4.45(d,2H), 5.01 (d,1H), 7.02–7.45(m,5H), 8.25(s,1H).

EXAMPLE 15

O-(N-Ethoxycarbonyl)thiocarbamoyl-N-(t-butyioxcarbonyll-(L-phenylalaninol

The procedure given in Example 14 was followed using N-(t-butyloxycarbonyl)-(L)-phenylalaninol as a starting material, instead of N-(t-butyloxycarbonyl)-(D)-phenylalaninol, to give 3.4 g of the title compound. A yield of 64% was obtained.

$_1$H-NMR(CDCl$_3$, 200 MHz), ppm($\delta$); 1.18–1.48(m,12H), 2.85–3.01(m,2H), 4.22–4.32(m,3H), 4.45(d,2H), 5.01(d, 1H), 7.12–7.35(m,5H), 8.28(s,1H).

EXAMPLE 16

3-N-(t-Butyloxycarbonyl)amino-3-phenyl-1-O-((N-methyl)thiocarbamoyl)propanol The procedure given in Example1 was followed using 3-N-t-butyloxycarbonyl)amino-3-phenyl-1-propanol as a starting material and methyl amine as a reactant instead of N-(t-butyloxycarbonyl)-(DL)-phenylalamniol and NH$_4$OH to give 3-N-(t-butyloxycarbonyl) amino-3-phenyl-1-O-((N-methyl)thiocarbamoyl)propanol. A yield of 70% was obtained.

$_1$H-NMR(CDCl$_3$, 200 MHz), ppm($\delta$); 1.18–1.48(m,9H), 2.68–32.92(m,3H), 3.02(d,2H), 4.01–4.18(m,1H), 4.29–4.48(m,2H), 4.85–4.92(m,1H), 6.81(br.,0.4H), 7.05–7.31(m,5H), 7.42(br.,0.6H).

EXAMPLE 17

3-N-(t-Butyloxycarbonyl)amino-2-phenyl-1-O-(thiocarbamoyl)propanol

The procedure given in Example 1 was followed using 3-N-(t-butyloxycarbonyl)amino-2-phenyl-1-propanol as a starting material instead of N-(t-butyloxycarbonyl)-(DL)-phenylalaninol, to give 3-N-(t-butyloxycarbonyl)amino-2-phenyl-1-O-(thiocarbamoyl) propanol. A yield of 66% was obtained.

$_1$H-NMR(CDCl$_3$, 200 MHz), ppm($\delta$); 1.42 (s, 9H), 3.21–3.40 (m, 2H), 3.55–3.68 (m, 1H), 4.50–4.70 (m, 3H), 6.20 (bs, 1H), 6.42 (bs, 1H), 7.20–7.40 (m, 5H)

EXAMPLE 18

3-N-(t-Butyloxycarbonyl)amino-2-phenyl-1-O-((N-methly)thiocarbamoyl)propanol The procedure given in Example 1 was followed using 3-N-(t-butyloxycarbonyl)amino-2-phenyl-1-propanol as a starting material and methyl amine as a reactant instead of N-(t-butyloxycarbonyl)-(DL)phenylaianinol and NH$_4$OH to give 3-N-(t-butyloxycarbonyl)amino-2-phenyl-1-O-((N-methyl)thiocarbamoyl)propanol. A yield of 92% was obtained.

$_1$H-NMR(CDCl$_3$, 200 MHz), ppm($\delta$, 1.40 (9H), 2.89 (1H), 3.06 (H), 3.13–3.45(2 H),3.45–3.72 (1H), 4.40–5.80 (2H), 6.30–6.70 (1H), 7.10–7.40 (5H)

EXAMPLE 19

3-N-(t-Butyloxycarbonyl)amino-2-phenyl-1-O-((N-dimethyl)thiocarbamoyl, propanol The procedure given in Example 1 was followed using 3-N-(t-butyloxycarbonyl)amino-2-phenyl-1-propanol as a starting material and dimethyl amine as a reactant instead of N-(t-butyloxycarbonyl)-(DL)-phenylalaninol and NH$_4$OH to give 3-N-(t-butyloxycarbonyl)amino- 2-phenyl-1-O-((N-dimethyl)thiocarbamoyl)propanol. A yield of 65% was obtained.

$_1$H-NMR(CDCl$_3$, 200 MHz), ppm($\delta$)1.41 (s,9H), 3.01 (s, 3H), 3.33 (3, 3H), 3.20–3.45 (m, 2H), 3.60 (m, 1H), 4.55–4.70 (m, 3H), 7.20–7.40 (m, 5H)

EXAMPLE 20

O-(N-Methyl)thiobiocarbanoyl-N-dimethyl-(D)-phenylalaninol

The procedure given in Example 3 was followed using N-dimethyl-D-phenylalaninol as a starting material and methylarine as a reactant, instead of N-(t-butyloxycarbonyl)-(D)-phenylalaniol and NH$_4$OH, to give 3.52 g of the title compound. A yield of 92% was obtained.

$_1$H-NMR(CDCl$_3$, 200 MHz), ppm($\delta$); 2.35(s,7.6H), 2.65–2.82(m,1.4H), 2.85–3.18(m,3H), 4.25–4.59(m,2H), 6.55(br,0.76H), 6.75(br,0.14H), 6.98–7.32(m,5H).

EXAMPLE 21

O-Thiocarbamoyl-(DL)-phenylalaninol Hydrochloride

In a 100 mL flask equipped with magnetic stirrer, O-thiocarbamoyl-N-(t-butyloxycarbonyl)-(DL)-phenylalaninol obtained in Example 1 was dissloved in 40 mL of THF and was added with 20 mL of 6N aqueous hydrochloric acid solution. The reaction mixture was stirred at room temperature for 8 hours, followed by the neutralization with saturated aqueous potassium carbonate solution. Thereafter, the organic layer was extracted 3 times with dichloromethane, dried over magnesium sulfate and distilled in vacuo, to give a yellowish liquid. This was dissolved in 30 mL of THF and added with anhydrous hydrochloric acid at 0° C., to obtained desirable white precipitates. To this was added 30 mL of anhydrous diethyl ether, with the aim of maximizing the precipitation. As a result, 1.32 g of the title compound was obtained: Yield 82%.

Melting point: 181.3–181.6° C.

$_1$H-NMR(DMSO-d$_6$, 200 MHz), ppm(δ); 2.78–3.18(m, 2H), 3.78–4.02(m, 1H), 4.15(d-d,1H), 4.37(d-d,1H), 7.08–7.45(m,5H), 8.38(br,4H), 9.02(s,1H).

EXAMPLE 22

O-Thiocarbamoyl-(L)-phenylalaninol Hydrochloride

The procedure given in Example 21 was followed using O-thiocarbamoyl-N-(t-butyloxycarbonyl)-(L)-phenylalaninol as a starting material, to give the title compound.

Melting point: 173.2–173.6° C.

$_1$H-NMR(DMSO-d$_6$, 200 MHz), ppm(δ); 2.78–3.15(m, 2H), 3.58–3.82(br,1H), 4.15(d-d,1H), 4.35(d-d,1H), 7.02–7.43(m,5H), 8.45(br,4H), 9.0(s,1H).

EXAMPLE 23

O-Thiocarbamoyl-(D)-phenylalaninol Hydrochloride

The procedure given in Example 21 was followed using O-thiocarbamoyl-N-(t-butyloxycarbonyl)-(D)-phenylalaninol as a starting material, to give the title compound.

Melting point: 181.5–181.7° C.

$_1$H-NMR(DMSO-d$_6$, 200 MHz), ppm(δ); 2.78–3.22(m, 2H), 3.58–3.82(br,1H), 4.08–4.48(m,2H), 7.12–7.58(m,5H), 8.45(br,4H), 9.05(s,1H).

EXAMPLE 24

O-(N-Methyl)thiocarbamoyl-(D)-phenylalaninol Hydrochloride

The procedure given in Example 21 was followed using O-(N-methyl)thiocarbamoyl-N-(t-butyloxycarboryl)-(D)-phenylalaninol as a starting material, to give the title compound.

Melting point: 1.78.1–179.5° C.

$_1$H-NMR(DMSO-d$_6$, 200 MHz), ppm(δ); 2.75–3.25(m, 5H), 3.65–3.95(br,1H), 4.11–4.55(m,2H), 7.18–7.61(m,5H), 7.48(br,3H), 9.25(d-d,1H).

EXAMPLE 25

O-(N-Cyloprrpyl)thiocarbamoyl-(D)-phenylalmninol Hydrochloride

The procedure given in Example 21 was followed using O-(N-cyclopropyl) thiocarbamoyl-N-(t-butyloxycarbonyl)-(D)-phenylalaninol as a starting material, to give the title compound.

Melting point: 180–181° C.

$_1$H-NM(DMSO-d$_6$, 200 MRz), ppm(δ); 0.45–0.91(m, 4H), 2.80–3.26(m,3H), 3.62–3.92(m,1H), 4.15–4.61 (m,2H), 7.18–7.58(m,5H), 8.45(br,3H), 9.45(d-d,1H).

EXAMPLE 26

O-(N-Octyl)thiocarbamoyl-(D)-phenylalaninol Hydrochloride

The procedure given in Example 21 was followed using O-(N-octyl)thiocarbamoyl-N-(t-butyloxycarbonyl)-(D)-phenylalaninol as a starting material, to give the title compound.

Melting point: 123–124° C.

$_1$H-NMR(DMSO-d$_6$, 200 MHz), ppm(δ); 0.89(t,3H), 1.12–1.68(m,14H), 2.78–3.35(m,4H), 3.75(br,1H), 4.01–4.82(m,4H), 7.05–7.48(m,5H), 8.52(br,3H), 9.32(d-d, 1H).

EXAMPLE 27

O-(N-Isopropyl)thiocarbamoyl-(D)-phenylalaninol Hydrochlonde

The procedure given in Example 21 was followed using O-(N-isopropyl) thiocarbamoyl-N-(t-butyloxycarbonyl)-(D)-phenylalaninol as a starting material, to give the title compound.

Melting point: 200.1–201° C.

$_1$H-NMR(DMSO-d$_6$, 200 MHz), ppm(δ) ; 1.05–1.45(m, 6H), 2.82–3.22(m,2H), 3.62–3.92(m,1H), 4.05–4.55(m,3H), 7.18–7.58(m,5H), 8.45(br,3H), 9.25(t,1H).

EXAMPLE 28

O-(N-Dimethyl)thiocarbamoyl-(D)-phenylalaninol Hydrochloride

The procedure given in Example 21 was followed using O-(N-dimethyl) thiocabamoyl-N-(t-butyloxycarbonyl)-(D)-phenylalaninol as a starting material, to give the title compound.

Melting point: 185.6–186.4° C.

$_1$H-NMR(DMSO-d$_6$, 200 MHz), ppm(δ); 2.75–3.55(m, 7H), 3.99(br.s,1H), 4.12–4.58(m,2H), 7.11–7.58(m,5H), 8.65(br,3H).

EXAMPLE 29

O-(N-Morpholino)thiocarbamoyl-(D)-phenylaianinol Hydrochloride

The procedure given in Example 21 was followed using O-(N-morpholino) thiocarbamoyl-N-(t-butyloxycarbonyl)-(D)-phenylaianinol as a starting material, to give the title compound.

Melting point: 202–203° C.

$_1$H-NMR(DMSO-d$_6$, 200 MHz), ppm(δ); 2.78–3.18(m, 2H), 3.38–4.08(m,11H), 4.18–4.53(m,2H), 7.18–7.48(m, 5H), 8.41(br,3H).

EXAMPLE 30

O-Thiocarbamoyl-(D)-(p-hydroxy)phenylalaninol Hydrochloride

The procedure given in Example 21 was followed using O-thiocarbanioyl-N-(t-butyloxycarbonyl)-(D)-(p-t-butyloxycarbonyloxy)phenylalaninol as a starting material, to give the title compound.

Melting point: 173.8–175.4° C.

$_1$H-NMR(DMSO-d$_6$, 200 MHz), ppm(δ); 2.68–3.18(m, 2H), 3.38–3.81(m,1H), 3.90–4.51(m,2H), 6.45–7.22(m,4H), 8.35(br,3H), 9.01(s,1H), 9.41(s,1H).

EXAMPLE 31

O-(N-Dimethyl)thiocarbamoyl-(D)-(3,4-dichloro) phenylalaninol Hydrochloride

The procedure given in Example 21 was followed using O-(N-dimethyl) thiocuamoyl-N-(t-butyloxycarbonyl)-(D)-

(m,p-dichloro)phenylalaninol as a starting material, to give the title compound.

Melting point: 189.7–190.3° C.

$_1$H-NMR(DMSO-d$_6$, 200 MHz), ppm(δ); 2.82–3.48(m, 8H), 3.72–3.94(m,1H), 4.25–4;59(m,2H), 7.32(d,1H), 7.52–7.75(m,2H), 8.35(br,3H).

EXAMPLE 32

O-(N-Methyl)thiocarbamoyl-(DL)-(o-fluoro) phenylalaninol Hydrochloride

The procedure given in Example 21 was followed using O-(N-methyl)thiocarbamoyl-N-(t-butyloxycarbonyl)-(DL)-(o-fluoro)phenylalaninol as a starting material, to give the title compound.

Meltingpoint: 169.6–170.2° C.

$_1$H-NMR(DMSO-d$_6$, 200 MHz), ppm(δ); 2.78(d-d,3H), 2.85–3.22(m,2H), 3.62–3.81(m,1H), 4.18(d-d,1H), 4.46(d-d,1H), 6.98–7.48(m,4H), 8.45(br,3H), 9.20(d-d,1H).

EXAMPLE 33

O-Thiocarbamoyl-(DL)-(p-chloro)phenylalaninol Hydrochloride

The procedure given in Example 21 was followed using O-thiocarbamoyl-N-(t-butyloxycarbonyl)-(DL)-(p-chloro) phenylalaninol as a starting material, to give the title compound.

Melting point: 187.5–187.7° C.

$_1$H-NMR(DMSO-d$_6$, 200 MHz), ppm(δ); 2.82–3.15(m, 2H), 3.62–3.82(m,i1H), 4.18(d-d,1H), 4.39(d-d,1H), 7.18–7.49(m,4H), 8.45(br,4H), 9.01(s,1H).

EXAMPLE 34

O-Ethoxycarbonyl)thiocarbamoyl-(D)-phenylalaninol Hydrochloride

The procedure given in Example 21 was followed using O-(N-ethoxyxcarbonyl) thiocarbamoyl-N-(t-butyloxycarbonyl)-(D)-phenylalaninol as a starting material, to give the title compound.

Melting point: 157–157.8° C.

$_1$H-NMR(DMSO-d$_6$, 200 MHz), ppm(δ); 1.22(t,3H), 2.78–3.18(m,2H), 3.82(br,1H) 4.22(q,3H), 4.58(d-d,1H), 7.18–7.45(m,5H), 8.42(br,3H), 11.78(s,1H).

EXAMPLE 35

O-(N-Ethoxycarbonyl)thiocarbamoyl-(L)-phenylalaninol Hydrochloride

The procedure given in Example 21 was followed using O-(N-ethoxycarbonyl) thiocarbamoyl-N-(t-butyloxycarbonyl)-(L)-phenylalaninol as a starting material, to give the title compound.

Melting point: 144.4–145.0° C.

$_1$H-NMR(DMSO-d$_6$, 200 MHz), ppm(δ); 1.22(t,3H), 2.78–3.18(m,2H), 3.62–3.92(m,1H), 3.95–4.38(m,3H), 4.42–4.62(m,1H), 7.02–7.45(m,5H), 8.42(br,3H), 11.85(s,1H).

EXAMPLE 36

3-Amino-3-phenyl-1-(O-(N-methyl)thiocarbamoyl) propanol Hydrochloride

The procedure given in Example 21 was followed using 3-N-(t-Butyloxycarbonyl) amino-3-phenyl-1-O-((N-methyl)thiocarbamoyl)-propanol as a starting material, to give the tide compound.

Melting Point: 182.1–182.4° C.

$_1$H-NMR(DMSO-d$_6$, 200 MHz), ppm(δ); 2.71–3.12(m, 3H), 3.22–3.48(m,2H), 3.75–3.95(m,1H), 4.18–4.62(m,2H), 7.25–7.62(m,5H), 8.25(br.,3H), 9.20(d,1H).

EXAMPLE 37

3-Amino-2-phenyl-1-(O-thiocarbamoyl)propanol Hydrochloride

The procedure given in Example 21 was followed using 3-N-(t-butyloxycarbonyl) amino-2-phenyl-1-O-(thiocarbamoyl)propanol as a starting material, to give the title compound.

Melting Point: 189.5–190.0° C.

$_1$H-NMR(DMSO-d$_6$, 200 MHz), ppm(δ); 3.05–3.50 (m, 3H), 4.35–4.55 (m, 2H), 7.30 (s, 5H), 7.95 (bs, 3H), 8.53 (s, 1H), 8.85 (s, 1H).

EXAMPLE 38

3-Amino-2-phenyl-1-O-((N-methyl)thiocarbamoyl) propanol Hydrochloride

The procedure given in Example 21 was followed using 3-N-(t-butyloxycarbonyl) amino-2-phenyl-1-O-((N-methyl) thiocarbamoyl)-propanol as a starting material, to give the title compound.

Melting Point: 95.0–96.0° C.

$_1$H-NMR(DMSO-d$_6$, 200 MHz), ppm(δ); 2.60 (d, 0.6H), 2.86 (d, 2.4H), 3.07–3.48 (m, 3H), 4.39–4.63 (m, 2H), 7.37 (s, 5H), 8.10 (bs, 3H), 9.15 (bs, 0.2H), 9.30 (bs, 0.8H)

EXAMPLE 39

3-Amino-2-phenyl-1-O-(N-dimethyl)thiocarbamoyl) propanol Hydrochloride

The procedure given in Example 21 was followed using 3-N-(t-butyloxycarbonyl)-amino-2-phenyl-1-O-((N-dimethyl)thiocubamoyl)propanol as a starting material, to give the title compound.

Melting Point: 164.1–164.6° C.

$_1$H-NMR(DMSO-d$_6$, 200 MHz), ppm(δ); 2.98 (s, 3H), 3.22 (s, 3H), 3.30–3.60 (m, 3H), 4.53 (m, 2H), 7.37 (m, 5H), 8.13 (bs, 3H)

EXAMPLE 40

O-(N-Methyl)thiocarbamoyl-N-dimethyl-(D)-phenylalaninol Hydrochloride

The procedure given in Example 21 was followed using O-(N-methyl) thiocarbamoyl-N-dimethyl-(D)-phenylalaninol as a starting material, to give the title compound.

Melting point: 152.5–152.7° C.

$_1$H-NMR(DMSO-d$_6$, 200 MHz), ppm(δ) ; 2.55–3.15(m, 9H), 3.15–3.45(m,2H), 3.75–4.02(m,1H), 4.15–4.71(m,2H), 7.05–7.58(m,5H), 9.25–9.65(m,1H), 11.05(br,1H).

The present invention has been described in an illustrative manner, and it is to be understood that the terminology used herein is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A racemic or enantiomerically enriched O-Thiocarbamoyl-aminoalkanol compound represented by the following structural formula (VI):

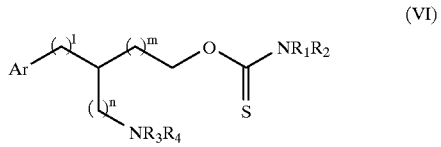

wherein Ar is a phenyl group as described as follows:

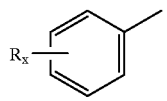

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an interger from 1 to 3, with the proviso that R is the same or different when x is 2 or 3, $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected each of l, m and n is zero or 1, and the pharmaceutically acceptable salts thereof.

2. The O-Thiocarbamoyl-aminoalkanol compound represented by the structural formula (VI), in accordance with claim 1, wherein R is hydrogen, and the pharmaceutically acceptable salts thereof.

3. The O-Thiocarbamoyl-aminoalkanol compound represented by the structural formula (VI), in accordance with claim 1, wherein R is hydrogen, $R_1$ and $R_2$ may be the same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atom substituted with a member selected from the group consisting of hydrogen, alkyl and aryl groups, or zero to one oxygen atom directly unconnected, $R_3$ and $R_4$ may be same or different from each other and are independently selected from the group consisting of hydrogen, lower alkyl of 1 to 8 carbon atoms, 3 to 7-membered aliphatic cyclic compounds $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atom directly unconnected, and the pharmaceutically acceptable salts thereof.

4. The O-Thiocarbamoyl-aminoalkanol compound represented by the structural formula (VI), in accordance with claim 1, wherein x is 1, and the pharmaceutically acceptable salts thereof.

5. An enantiomerically enriched O-Thiocarbamoyl-(D)-aminoalkanol compound represented by the following structural formla (VIII):

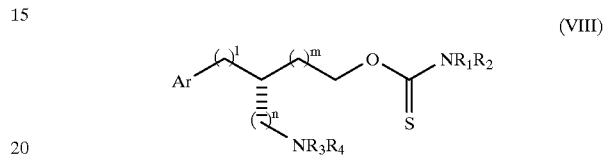

wherein Ar is a phenyl group as described as follows:

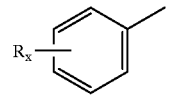

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, each of l, m and n is zero or 1, and the pharmaceutically acceptable salts thereof.

6. The O-Thiocarbamoyl-aminoalkanol compound represented by the structural formula (VIII), in accordance with claim 5, wherein R is hydrogen, and the pharmaceutically acceptable salts thereof.

7. The O-Thiocarbamoyl-aminoalkanol compound represented by the structural formula (VIII), in accordance with claim 5, wherein R is hydrogen, $R_1$ and $R_2$ may be the same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atom substituted with a member selected from the group consisting of hydrogen, alkyl and aryl groups, or zero to one oxygen atom directly unconnected, $R_3$ and $R_4$ may be same or different from each other and are independently selected from the group consisting of hydrogen, lower alkyl of 1 to 8 carbon atoms; 3 to 7-membered aliphatic cyclic compounds and $R_3$ and $R_4$, together with the adjoining N-atom, form a 5 to 7-membered cyclic compound which optionally comprises zero to one additionalnitrogen atoms substituted with a member selected from the group consisting of hydrogen, alkyl and aryl groups, or zero to one oxygen atoms directly unconnected, and the pharmaceutically acceptable salts thereof.

8. The O-Thiocarbamoyl-aminoalkanol compound represented by the structural formula (VIII), in accordance with claim 5, wherein x is 1, and the pharmaceutically acceptable salts thereof.

9. An enantiomerically enriched O-Thiocarbamoyl-(L)-atninoalkanol compound represented by the following structural formula (IX):

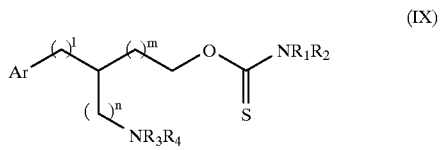

(IX)

wherein Ar is a phenyl group as described as follows:

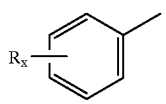

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and, $R_3$ and $R_4$ together with the adjoining N-atom, form a 5 to 7-membered cyclic compound which optionally comprises zero to one additional nitrogen atom substituted with a member selected from the group consisting of hydrogen, alkyl and aryl groups, or zero to one oxygen atoms directly unconnected, each of l, m and n is zero or 1, and the pharmaceutically acceptable salts thereof.

10. The O-Thiocarbamoyl-aminoalkanol compound represented by the structural formula (IX), in accordance with claim 9, wherein R is hydrogen, and the pharmaceutically acceptable salts thereof.

11. The O-Thiocarbamoyl-aminoalkanol compound represented by the structural formula (IX), in accordance with claim 9, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

12. The O-Thiocarbamoyl-aminoalkanol compound represented by the structural formula (IX), in accordance with claim 9, wherein x is 1, and the pharmaceutically acceptable salts thereof.

13. A racemic or enantiomerically enriched O-Thiocarbamoyl-aminoalkanol compound represented by the following structural formula (X):

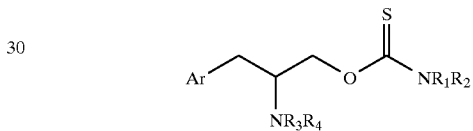

(X)

wherein Ar is a phenyl group as described as follows:

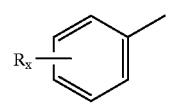

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

14. The O-Thiocarbamoyl-aminoalkanol compound represented by the structural formula (X), in accordance with claim 13, wherein R is hydrogen, and the pharmaceutically acceptable salts thereof.

15. The O-Thiocarbamoyl-aminoalkanol compound represented by the structural formula (X), in accordance with claim 13, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

16. The O-Thiocarbamoyl-aminoalkanol compound represented by the structural formula (X), in accordance with claim 13, wherein x is 1, and the pharmaceutically acceptable salts thereof.

17. An enantiomerically enriched O-Thiocarbamoyl-(D)-aminoalkanol compound represented by the following structural formula (XI):

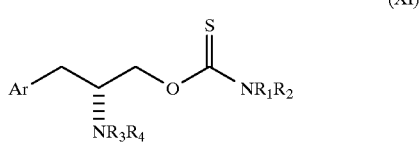

(XI)

wherein Ar is a phenyl group as described as follows:

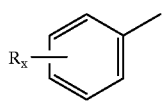

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups or zero to one oxygen atoms directly unconnected, and the pharmaceutically acceptable salts thereof.

18. The O-Thiocarbamoyl-aminoalkanol compound represented by the structural formula (XI), in accordance with claim 17, wherein R is hydrogen, and the pharmaceutically acceptable salts thereof.

19. The O-Thiocarbamoyl-aminoalkanol compound represented by the structural formula (XI), in accordance with claim 17, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group-consisting of hydrogen, and aryl groups, or zero to one oxygen atoms directly unconnected, and the pharmaceutically acceptable salts thereof.

20. The O-Thiocarbamoyl-aminoalkanol compound represented by the structural formula (XI), in accordance with claim 17, wherein x is 1, and the pharmaceutically acceptable salts thereof.

21. An enantiomerically enriched O-Thiocarbamoyl-(L)-aminoalkanol compound represented by the following structural formula (XII):

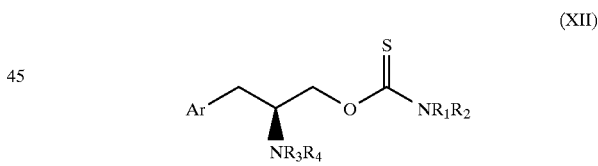

(XII)

wherein Ar is a phenyl group as described as follows:

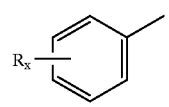

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

22. The O-Thiocarbamoyl-aminoalkanol compound represented by the structural formula (XII), in accordance with claim 21, wherein R is hydrogen, and the pharmaceutically acceptable salts thereof.

23. The O-Thiocarbamoyl-aminoalkanol compound represented by the structural formula (XII), in accordance with claim 21, wherein R is hydrogen, $R_1$ and $R_2$ may be the same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

24. The O-Thiocarbamoyl-aminoalkanol compound represented by the structural formula (XII), in accordance with claim 21, wherein x is 1, and the pharmaceutically acceptable salts thereof.

25. A racemic or enantiomerically enriched O-Thiocarbamoyl-aminoalkanol compound represented by the following structural formula (XIII):

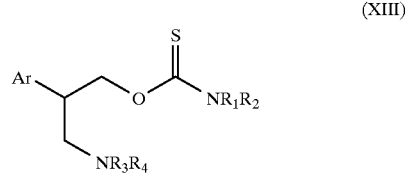

(XIII)

wherein Ar is a phenyl group as described as follows:

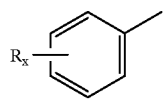

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

26. The O-Thiocarbamoyl-aminoalkanol compound represented by the structural formula (XIII), in accordance with claim 25, wherein R is hydrogen, and the pharmaceutically acceptable salts thereof.

27. The O-Thiocarbamoyl-aminoalkanol compound represented by the structural formula (XIII), in accordance with claim 25, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the-group consisting of hydrogen, alkyl and aryl groups, or zero to one oxygen atoms directly unconnected, and the pharmaceutically acceptable salts thereof.

28. The O-Thiocarbamoyl-aminoalkanol compound represented by the structural formula (XIII), in accordance with claim 25, wherein x is 1, and the pharmaceutically acceptable salts thereof.

29. An enantiomerically enriched O-Thiocarbamoyl-(D)-aminoalkanol compound represented by the following structural formula (XIV):

(XIV)

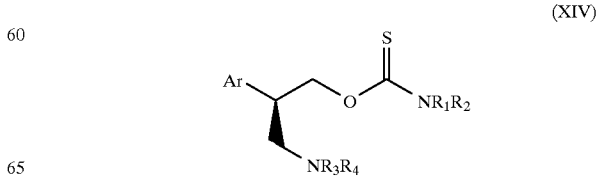

wherein Ar is a phenyl group as described as follows:

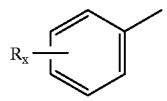

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms 5substituted with a member selected from the group consisting of hydrogen, alkyl and aryl groups, or zero to one oxygen atoms directly unconnected, and the pharmaceutically acceptable salts thereof.

30. The O-Thiocarbamoyl-aminoalkanol compound represented by the structural formula (XIV), in accordance with claim 29, wherein R is hydrogen, and the pharmaceutically acceptable salts thereof.

31. The O-Thiocarbamoyl-aminoalkanol compound represented by the structural formula (XIV), in accordance with claim 29, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to, 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

32. The O-Thiocarbamoyl-aminoalkanol compound represented by the structural formula (XIV), in accordance with claim 29, wherein x is 1, and the pharmaceutically acceptable salts thereof.

33. An enantiomerically enriched O-Thiocarbamoyl-(L)-aminoalkanol compound represented by the following structural formula (XV):

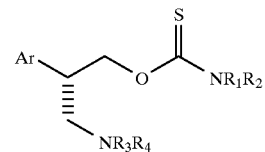

(XV)

wherein Ar is a phenyl group as described as follows:

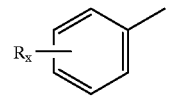

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

34. The O-Thiocarbamoyl-aminoalkanol compound represented by the structural formula (XV), in accordance with claim 33, wherein R is hydrogen, and the pharmaceutically acceptable salts thereof.

35. The O-Thiocarbamoyl-aminoalkanol compound represented by the structural formula (XV), in accordance with claim 33, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

36. The O-Thiocarbamoyl-aminoalkanol compound represented by the structural formula (XV), in accordance with claim 33, wherein x is 1, and the pharmaceutically acceptable salts thereof.

37. A racemic or enantiomerically enriched O-Thiocarbamoyl-aminoalkanol compound represented by the following structural formula (XVI):

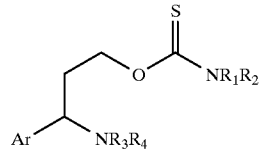
(XVI)

wherein Ar is a phenyl group as described as follows:

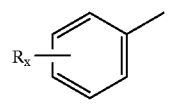

wherein R is a member selected from the group consisting of hydrogen, lower alkyl of 1 to 8 carbon atoms, halogens selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyd of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

38. The O-Thiocarbamoyl-aminoalkanol compound represented by the structural formula (XVI), in accordance with claim 37, wherein R is hydrogen, and the pharmaceutically acceptable salts thereof.

39. The O-Thiocarbamoyl-aminoalkanol compound represented by the structural formula (XVI), in accordance with claim 37, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together,with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ maybe same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the phraceuticlly acceptable salts thereof.

40. The O-Thiocarbamoyl-aminoalkanol compound represented by the structural formula (XVI), in accordance with claim 37, wherein x is 1, and the pharmaceutically acceptable salts thereof.

41. An enantiomerically enriched O-Thiocabamoyl-(D)-aminoalkanol compound resented by the following structural formula (XVII):

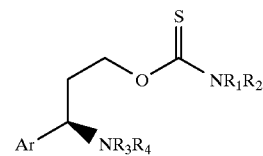
(XVII)

wherein Ar is a phenyl group as described as follows:

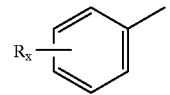

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

42. The O-Thiocarbamoyl-aminoalkanol compound represented by the structural formula (XVII), in accordance with claim 41, wherein R is hydrogen, and the pharmaceutically acceptable salts thereof.

43. The O-Thiocarbamoyl-aminoalkanol compound represented by the structural formula (XVII), in accordance with claim 41, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

44. The O-Thiocarbamoyl-aminoalkanol compound represented by the structural formula (XVII), in accordance with claim 41, wherein x is 1, and the pharmaceutically acceptable salts thereof.

45. An enantiomerically enriched O-Thiocarbamoyl-(L)-aminoalkanol compound represented by the following structural formula (XVIII):

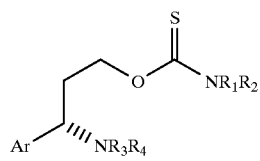

(XVIII)

wherein Ar is a phenyl group as described as follows:

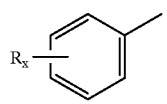

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3. $R_1$ and $R_2$ may be the same or different from each other and are independently selected from the group consisting of hydrogen, lower alkyl of 1 to 8 carbon atom, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

46. The O-Thiocarbamoyl-aminoalkanol compound represented by the structural formula (XVIII), in accordance with claim 45, wherein R is hydrogen, and the pharmaceutically acceptable salts thereof.

47. The O-Thiocarbamoyl-aminoalkanol compound represented by the structural formula (XVIII), in accordance with claim 45, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms diretly unconnected wanted, and the pharmaceutically acceptable salts thereof.

48. The O-Thiocarbamoyl-aminoalkanol compound represented by the structural formula (XVIII), in accordance with claim 45, wherein x is 1, and the pharmaceutically acceptable salts thereof.

49. A racemic or enantiomerically enriched O-Thiocarbamoyl-aminoalkanol compound resented by the following structural formula (XIX):

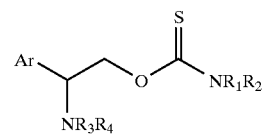

(XIX)

wherein Ar is a phenyl group as described as follows:

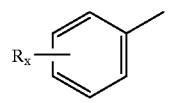

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be the same or different from each other and arm independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl grups or zero to one oxygen atoms directly unconnected, and the pharmaceutically acceptable salts thereof.

50. The O-Thiocarbamoyl-aminoalkanol compound represented by the structural formula (XIX), in accordance with claim 49, wherein R is hydrogen, and the pharmaceutically acceptable salts thereof.

51. The O-Thiocarbamoyl-aminoalkanol compound represented by the structural formula (XIX), in accordance with claim 49, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

52. The O-Thiocarbarnoyl-aminoalkanol compound represented by the structural formula (XIX), in accordance with claim 49, wherein x is 1, and the pharmaceutically acceptable salts thereof.

53. An enantiomerically enriched O-Thiocarbamoyl-(D)-aminoalkanol compound represented by the following structural formula (XX);

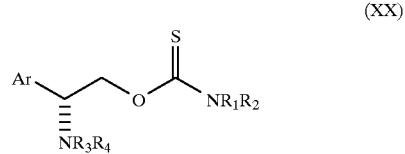

(XX)

wherein Ar is a phenyl group as described as follows:

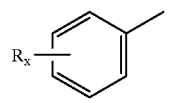

wherein R is a member selected from the group consisting of hydrogen, lower alkyl of 1 to 8 carbon atoms, halogen selected from F, Cl Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be the same or different from each other and are independently selected from the group consisting of hydrogen, lower alkyl of 1 to 8 carbon atoms, aryl 3 to 7-membered aliphatic cyclic compounds and $R_1$ and $R_2$, together with the-adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

54. The O-Thiocarbarnoyl-aminoalkanol compound represented by the structural formula (XX), in accordance with claim 53, wherein R is hydrogen, and the pharmaceutically acceptable salts thereof.

55. The O-Thiocarbamoyl-aminoalkanol compound represented by the structural formula (XX), in accordance with claim 53, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

56. The O-Thiocarbamoyl-aminoalkanol compound represented by the structural formula (XX), in accordance with claim 53, wherein x is 1, and the pharmaceutically acceptable salts thereof.

57. An enantiomerically enriched O-Thiocarbarnoyl-(L)-aminoalkanol compound represented by the following structural formula (XXI):

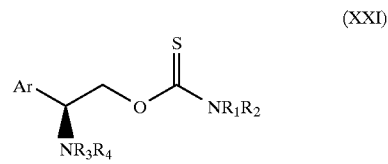

(XXI)

wherein Ar is a phenyl group as described as follows:

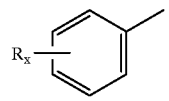

wherein R is a member selected from the group consisting of hydrogen, lower alkyl of 1 to 8 carbon atoms, halogen selected from F, Cl, Br, and I, alkoxy containing 1 to 3 carbon atoms, thioalkoxy containing 1 to 3 carbon atoms, nitro, hydroxy, or trifluorocarbon, and x is an integer from 1 to 3, with the proviso that R is the same or different when x is 2 or 3, $R_1$ and $R_2$ may be the same or different from, each other and are independently selected from the group consisting of hydrogen, lower alkyl of 1 to 8 carbon atoms, aryl, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, aryl, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

58. The O-Thiocarbamoyl-aminoalkanol compound represented by the structural formula (XXI), in accordance with claim 57, wherein R is hydrogen, and the pharmaceutically acceptable salts thereof.

59. The O-Thiocarbamoyl-aminoalkanol compound represented by the structural formula (XXI), in accordance with claim 57, wherein R is hydrogen, $R_1$ and $R_2$ may be same or different from each other and are independently selected from the group consisting of hydrogen, lower alkyl of 1 to 8 carbon atoms, 3 to 7-membered aliphatic cyclic compounds and $R_1$ and $R_2$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, $R_3$ and $R_4$ may be same or different from each other and are independently selected from the group consisting of hydrogen, lower alkyl of 1 to 8 carbon atoms, 3 to 7-membered aliphatic cyclic compounds and $R_3$ and $R_4$, together with the adjoining N-atom, form a 5 to 7-membered cyclic compound which optionally comprises zero to one additional nitrogen atoms substituted with a member selected from the group consisting of hydrogen, alkyl and aryl groups, or zero to one oxygen atoms directly unconnected, and the pharmaceutically acceptable salts thereof.

60. The O-Thiocarbamoyl-aminoalkanol compound represented by the structural formula (XXI), in accordance with claim 57, wherein x is 1, and the pharmaceutically acceptable salts thereof.

61. A method for the preparation of a compound of formula (VI) as defined in claim 1, in which an aminoalkanol of general formula (II)

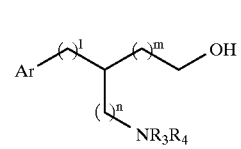

is reacted with Di-t-butyl dicarbonate to synthesize N-t-butyloxycarbonyl-aminoalkanol represented by the formula (III),

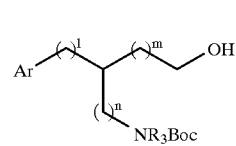

followed by the treatment with sodium hydride, carbon disulfide and methyl iodide in an ethereal solution, which is followed by the treatment with an amine compound of formula (IV)

$$HNR_1R_2 \qquad (IV)$$

to yield O-thiocarbamoyl-N-t-butyloxycarbonyl-aminoalkanol represented by general formula(V),

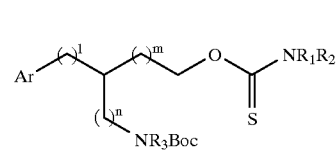

wherein Ar, $R_1$, $R_2$, $R_3$, $R_4$, l, m and n are as defined above claim 1 and Boc repressants t-butyloxy carbonyl radical, which is deprotected by aqueous hydrochloric acid solution to give a O-thiocarbamoyl-aminoalkanol represented by the general formula (VI)

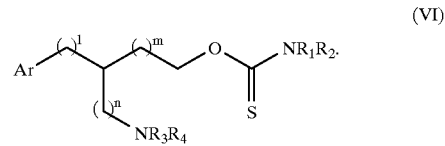

62. The method of claim 61 wherein without further purification, the compound of formula (VI) may be converted into its pharmaceutically acceptable salts, formula (I)

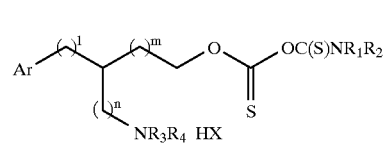

63. A method for the preparation of a compound of formula (VI) wherein as defined in claim 1, in which an aminoalkanol of general formula (II) wherein $R_3$ and $R_4$ are not hydrogen

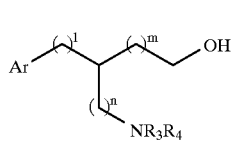

is reacted with sodium hydride, carbon disulfide and methyl iodide in an etheral solution which is followed by the treatment with an amine compound of formula (IV)

HNR$_1$R$_2$ (IV)

to yield O-thiocarbamoyl-aminoalkanol represented by the general formula (VI)

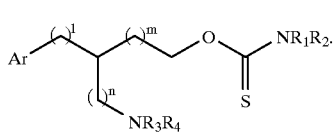

64. The method of claim 63 wherein without further purification, the compound of formula (VI) may be converted into its pharmaceutically acceptable salts, formula (I)

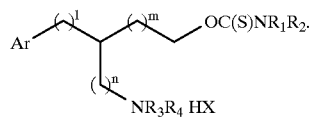

65. A method for the preparation of a compound of formula (VI) as defined in claim 1, in which an aminoalkanol of general formula (II) wherein R$_1$=H

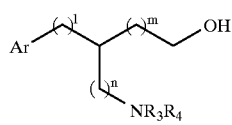

is reacted with Di-t-butyl dicarbonate to synthesize N-t-butyloxycarbonyl-aminoalkanol represented by the formula (III),

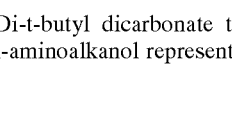

followed by the treatment with isothiocyanate compound of formula (VII)

R$_2$NCS (VII)

in an halogenated hydrocarbon solution to yield O-thiocarbamoyl-N-t-butyloxycarbonyl-aminoalkanol represented by general formula (V),

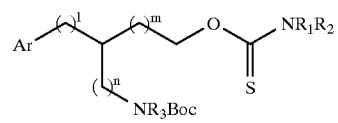

wherein Ar, R$_1$, R$_2$, R$_3$, R$_4$, l, m and n are as defined above claim 1 and Boc repressants t-butyloxy carbonyl radical, which is deprotected by aqueous hydrochloric acid solution to give a O-thiocarbamoyl-aminoalkanol represented by the general formula (VI)

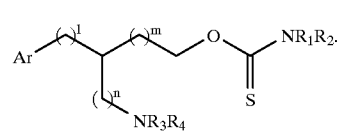

66. The method of claim 65 wherein without further purification, the compound of formula (VI) may be converted into its pharmaceutically acceptable salts, formula (I)

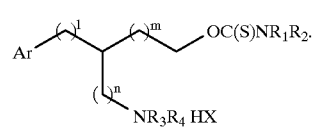

67. A method for the preparation of a compound of formula (VI) wherein as defined in claim 1, in which an aminoalkanol of general formula (II) wherein R$_3$ and R$_4$ are not hydrogen

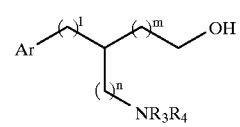

is reacted with isothiocyanate compound of formula (VII)

R$_2$NCS (VII)

in an halogenated hydrocarbon solution to yield a O-thiocarbamoyl-aminoalkanol represented by the general formula (VI)

68. The method of claim 67, wherein without further purification, the compound of formula (VI) may be converted into its pharmaceutically acceptable salts, formula (I)

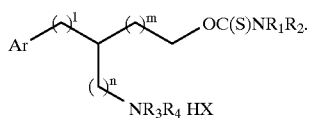

(I)

69. A method for the preparation of a compound of formula (VIII) according to claim 61 in which an (D)-aminoalkanol is employed.

70. A method for the preparation of a compound of formula (VIII) according to claim 63 in which an (D)-aminoalkanol is employed.

71. A method for the preparation of a compound of formula (VIII) according to claim 65 in which an (D)-aminoalkanol is employed.

72. A method the preparation of a compound of formula (VIII) according to claim 67 in which an (D)-aminoalkanol employed.

73. A method for the preparation of a compound of formula (IX) according to claim 61 in which an (L)-aminoalkanol is employed.

74. A method for the preparation of a compound of formula (VIII) according to claim 63 in which an (L)-aminoalkanol is employed.

75. A method for the preparation of a compound of formula (VIII) according to claim 65 in which an (L)-aminoalkanol is employed.

76. A method for the preparation of a compound of formula (VIII) according to claim 67 in which an (L)-aminoalkanol is employed.

77. A pharmaceutical composition, comprising a compound of formula (VI) or a pharmaceutically acceptable salt thereof as claimed in claime 1, together with a non-toxic pharmaceutically acceptable carrier or diluent therefor.

78. A pharmaceutical composition, comprising a compound of formula (VIII) or a pharmaceutically acceptable salt thereof as claimed in clime 5, together with a non-toxic pharmaceutically acceptable carrier or diluent therefor.

79. A pharmaceutical composition, comprising a compound of formula (IX) or a pharmaceutically acceptable salt thereof as claimed in claim 9, together with a non-toxic pharmaceutical acceptable carrier or diluent therefor.

80. A method of treating a mammal suffering from a disorder of the central nervous system which comprises administering to said mammal a central nervous system dosage effective amount of the compound of claim 1.

81. A method of treating a mammal suffering from a disorder of the central nervous system which comprises administering to said mammal a central nervous system dosage effective amount of the compound of claim 5.

82. A method of treating a mammal suffering from a disorder of the central nervous system which comprises administering to said mammal a central nervous system dosage effective amount of the compound of claim 9.

83. A compound selected from the group consisting of O-Thiocarbamoyl-(DL)-phenylalaninol, O-Thiocarbamoyl-(D)-phenylalninol, and O-Thiocarbamoyl-(L)-phenylalaninol; and non-toxic pharmacologically acceptable salts thereof.

84. O-Thiocarbamoyl-(D)-phenylalaninol; and non-toxic pharmacologically acceptable salts thereof.

85. O-Thiocarbamoyl-(L)-phenylalaninol; and non-toxic pharmacologically acceptable salts thereof.

86. A method of treating a mammal suffering from disorder of the central nervous system which comprises administering to said mammal a central nervous system dosage effective amount of the compound of claim 83.

87. A method of treating a mammal suffering from disorder of the central nervous system which comprises administering to said mammal a central nervous system dosage effective amount of the compound of claim 84.

88. A method of treating a mammal suffering from disorder of the central nervous system which comprises administering to said mammal a central nervous system dosage effective amount of the compound of claim 85.

* * * * *